(12) United States Patent
Taarning et al.

(10) Patent No.: US 8,143,439 B2
(45) Date of Patent: Mar. 27, 2012

(54) ZEOLITE-CATALYZED PREPARATION OF ALPHA-HYDROXY CARBOXYLIC ACIDS AND ESTERS THEREOF

(75) Inventors: Esben Taarning, Copenhagen S (DK); Saravanamurugan Shunmugavel, Lyngby (DK); Martin Spangsberg Holm, Copenhagen (DK)

(73) Assignee: Haldor Topsøe A/S, Lyngby (DK)

( * ) Notice: Subject to any disclaimer, the term of this patent is extended or adjusted under 35 U.S.C. 154(b) by 173 days.

(21) Appl. No.: 12/614,251

(22) Filed: Nov. 6, 2009

(65) Prior Publication Data

US 2010/0121096 A1    May 13, 2010

(30) Foreign Application Priority Data

Nov. 11, 2008 (DK) ................... 2008 01556
Jun. 19, 2009 (DK) ................... 2009 00757

(51) Int. Cl.
  *C07C 69/66* (2006.01)
  *C07C 59/08* (2006.01)

(52) U.S. Cl. .............................. 560/179; 562/589

(58) Field of Classification Search .............. None
  See application file for complete search history.

(56) References Cited

U.S. PATENT DOCUMENTS
6,306,364 B1  10/2001  Valencia et al.

FOREIGN PATENT DOCUMENTS

| CN | 101265180 A | | 9/2008 |
|---|---|---|---|
| CN | 101270043 A | * | 9/2008 |
| CN | 101270043 A | | 9/2008 |
| JP | 2008-120796 A | | 5/2008 |

OTHER PUBLICATIONS

White et al, Basic Energy Sciences Advisory Committee Subpanel Workshop Report, Opportunities for Catalysis in the 21st Century, 2002, pp. 1-47.*
Zhang et al, Gongye Cuiha, Hydrolysis of Glucose Over Environmentally-benign Catalysts, 2006, 14(5), pp. 27-29, English Abstrac.*
T. Blasco, et al., "Unseeded Synthesis of Al-free Ti-β Zeolite in Fluoride Medium: A Hydrophobic Selective Oxidation Catalyst," *Chemical Communications*, pp. 2367-2368, 1996.
N.K. Mal, et al., "Sn-MFI Molecular Sieves: Synthesis Methods, $^{29}$Si Liquid and Solid MAS-NMR, $^{119}$Sn Static and MAS NMR Studies," *Microporous Materials*, vol. 12, pp. 331-340, 1997.
S. Saravanamurugan, et al., "Liquid-Phase Reaction of 2'-Hydroxyacetophenone and Benzaldehyde Over $SO_3H$-SBA-15 Catalysts: Influence of Microwave and Thermal Effects," *Microporous and Mesoporous Materials*, vol. 112, pp. 97-107, 2008.
Y. Zhu, et al., "Al-Free Zr-Zeolite Beta as a Regioselective Catalyst in the Meerwein-Ponndorf-Verley Reaction," *Chemical Communications*, pp. 2734-2735, 2003.
Y. Zhu, et al., "Chemo- and Regioselective Meerwin-Ponndorf-Verley and Oppenauer Reactions Catalyzed by Al-free Zr-Zeolite Beta," *Journal of Catalysis*, vol. 227, pp. 1-10, 2004.
M. Bicker et al., "Catalytical Conversion of Carbohydrates in Subcritical Water: A New Chemical Process for Lactic Acid Production." Journal of Molecular Catalysis A: Chemical 239, pp. 151-157, 2005.

\* cited by examiner

*Primary Examiner* — Paul A Zucker
(74) *Attorney, Agent, or Firm* — Dickstein Shapiro LLP

(57) ABSTRACT

A process for the production of lactic acid and 2-hydroxy-3-butenoic acid or esters thereof by conversion of glucose, fructose, sucrose, xylose and glycolaldehyde dissolved in a solvent in presence of a solid Lewis acidic catalyst.

6 Claims, No Drawings

ZEOLITE-CATALYZED PREPARATION OF ALPHA-HYDROXY CARBOXYLIC ACIDS AND ESTERS THEREOF

The present invention relates to the preparation of α-hydroxy carboxylic acid compounds by catalytic conversion of carbohydrates and carbohydrate like material. In particular, the invention is a process for the preparation of lactic acid compounds as main product and 2-hydroxy-3-butenoic acid as valuable by-product from glucose, fructose, sucrose, xylose or glycolaldehyde in presence of a solid Lewis acidic zeolite.

Lactic acid is an important chemical that is used for production of biodegradable polymers and solvents. The industrial production of lactic acid is based on the anaerobic fermentation of glucose and sucrose using microbial fermentation. The major complications associated with this process are the need to neutralize lactic acid with a stoichiometric amount of base during the fermentation process and the energy intensive work-up of lactic acid from the aqueous fermentation broth.

We have now found that Lewis acidic zeolites such as Sn-Beta show surprisingly high activity and selectivity for the conversion of carbohydrates or carbohydrate like compounds such as sucrose, glucose, fructose, xylose and glycolaldehyde to esters of lactic acid and 2-hydroxy-3-butenoic acid according the following reaction scheme:

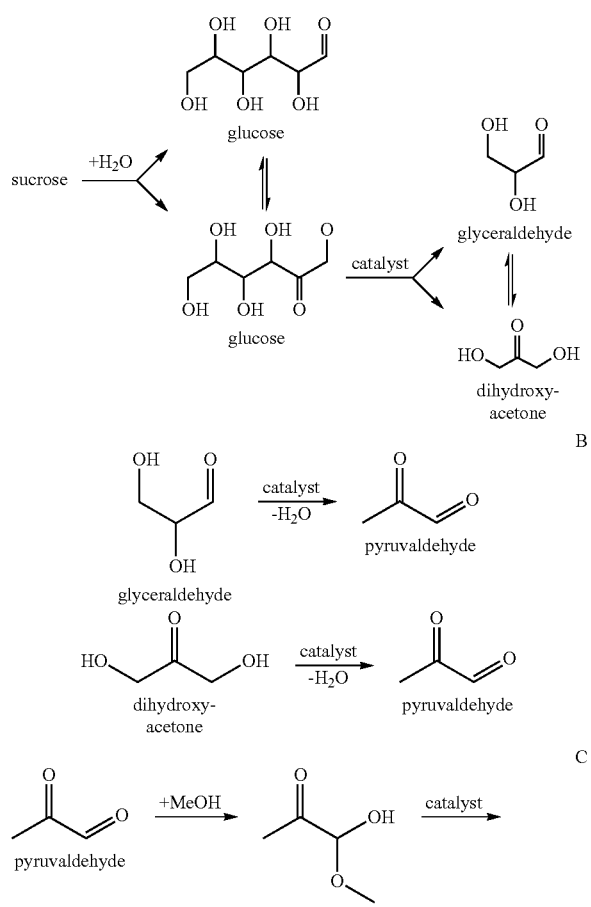

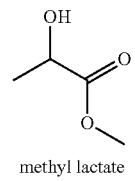

methyl lactate

Part A: hydrolysis of sucrose and fragmentation to form triose sugars (dihydroxyacetone and glyceraldehyde). Part B: dehydration of the triose sugars to form methyl glyoxal. Part C: addition of methanol to methyl glyoxal to form a hemiacetal followed by redox isomerisation of the hemiacetal to produce methyl lactate.

Pursuant to the above finding this invention is a process for the production of lactic acid and 2-hydroxy-3-butenoic acid or esters thereof by conversion of glucose, fructose, sucrose, xylose or glycolaldehyde dissolved in a solvent in presence of a solid Lewis acidic catalyst.

A useful solid Lewis acidic catalyst is a zeotype material, preferably containing a tetravalent metal being incorporated in its framework, such as Sn, Pb, Ge, Ti, Zr and/or Hf. Most preferably, the zeotype material contains tetravalent Sn and/or Ti.

The zeotype material has preferably a structure type BEA, MFI, MEL, MTW, MOR, LTL or FAU, such as zeolite beta and ZSM-5. A further preferred zeotype materiel is TS-1. Further useful catalysts are Lewis acidic mesoporous amorphous materials, preferably with the structure type MCM-41 or SBA-15.

Lactic acid and 2-hydroxy-3-butenoic acid are prepared in an aqueous solution of the sugars containing the catalyst. When the desired products are the esters of the acids, the solvent is an alcohol, such as methanol and ethanol, optionally admixed with a secondary solvent.

The secondary solvent may be water, dimethyl sulfoxide or a hydrocarbon solvent.

Higher esters of lactic acid and 2-hydroxy-3-butenoic acid may be prepared by use of higher alcohols as solvent. For example, ethyl lactate and ethyl 2-hydroxy-3-butenoate are prepared by using ethanol and/or a mixture of ethanol and a secondary solvent, such water in the case of 96% ethanol. Similarly, i-propyl esters are prepared when 2-propanol is used as the solvent and the n-butyl esters are prepared by use of 1-butanol as the solvent.

The above reactions according to the invention may be conducted in a batch or flow reactor at temperatures in the range of 50-300° C., preferably 100-220° C. and most preferred between 140 and 200° C.

EXAMPLES

Examples 1-5 illustrate a process for the conversion of sucrose, glucose, fructose, xylose and glycolaldehyde in methanol to form methyl lactate and methyl 2-hydroxy-3-butenoate using Sn-BEA as the catalyst.

Example 1

An autoclave (50 cc microclave) is charged with 8.0 g of methanol, 0.2250 g of sucrose (0.6576 mmol), 121.3 mg naphthalene (internal standard) and finally with 160.2 mg Sn-BEA (prepared according to U.S. Pat. No. 6,306,364). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 1.74 mmol of methyl lactate is formed (66%) together with 0.022 mmol methyl 2-hydroxy-3-butenoate (1%).

Example 2

An autoclave (50 cc microclave) is charged with 8.0 g of methanol, 0.2251 g of glucose (1.250 mmol), 119.3 mg naphthalene (internal standard) and finally with 160.3 mg Sn-BEA (prepared according to U.S. Pat. No. 6,306,364). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 1.02 mmol of methyl lactate is formed (41%) together with 0.051 mmol methyl 2-hydroxy-3-butenoate (3%).

Example 3

An autoclave (50 cc microclave) is charged with 8.0 g of methanol, 0.2251 g of fructose (1.250 mmol), 120.0 mg naphthalene (internal standard) and finally with 162.0 mg Sn-BEA (prepared according to U.S. Pat. No. 6,306,364). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 1.07 mmol methyl lactate is formed (43%) together with 0.068 mmol methyl 2-hydroxy-3-butenoate (4%).

Example 4

An autoclave (50 cc microclave) is charged with 8.0 g of methanol, 0.2251 g of xylose (1.500 mmol), 121.8 mg naphthalene (internal standard) and finally with 160.0 mg Sn-BEA (prepared according to U.S. Pat. No. 6,306,364). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 0.75 mmol of methyl lactate is formed (30%) together with 0.049 mmol methyl 2-hydroxy-3-butenoate (3%).

Example 5

An autoclave (50 cc microclave) is charged with 8.0 g of methanol, 0.2254 g of glycolaldehyde (3.755 mmol), 119.5 mg naphthalene (internal standard) and finally with 160.0 mg Sn-BEA (prepared according to U.S. Pat. No. 6,306,364). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 0.40 mmol of methyl lactate is formed (16%) together with 0.47 mmol methyl 2-hydroxy-3-butenoate (25%).

Examples 6-9 illustrate the use of different Lewis acidic catalysts in a process for the conversion of sucrose in methanol to form methyl lactate and methyl 2-hydroxy-3-butenoate.

Example 6

An autoclave (50 cc microclave) is charged with 8.0 g of methanol, 0.2251 g of sucrose (0.6575 mmol), 121.0 mg naphthalene (internal standard) and finally with 160.0 mg Sn-MFI (prepared according to method A in Mal et al, *Micro. Mater.*, 12, 1997, 331-340). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 0.973 mmol of methyl lactate is formed (37%) together with 0.006 mmol methyl 2-hydroxy-3-butenoate (0.3

Example 7

An autoclave (50 cc microclave) is charged with 8.0 g of methanol, 0.2247 g of sucrose (0.6564 mmol), 111.5 mg naphthalene (internal standard) and finally with 165.1 mg Sn-SBA-15 (prepared according to *Micro. Meso. Mater.*, 112, 2008, 97 using $SnCl_4 \cdot 5H_2O$ as the tin source). The autoclave is closed, charged with 20 bar of argon and heated to 160° C. After the temperature reaches 100° C., the mechanical stirrer is started (500 rpm) and the mixture is heated for hours under these conditions. GC-analysis of the reaction mixture shows that 0.55 mmol of methyl lactate is formed (21%) together with 0.002 mmol methyl 2-hydroxy-3-butenoate (0.1%).

Example 8

An autoclave (50 cc microclave) is charged with 8.0 g of methanol, 0.2261 g of sucrose (0.6605 mmol), 118.3 mg naphthalene (internal standard) and finally with 160.2 mg Zr-BEA (prepared according to *Chem Commun*, 2003, 2734). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 0.977 mmol of methyl lactate is formed (37%) together with 0.036 mmol methyl 2-hydroxy-3-butenoate (2%).

Example 9

An autoclave (50 cc microclave) is charged with 8.0 g of methanol, 0.2255 g of sucrose (0.6587 mmol), 120.0 mg naphthalene (internal standard) and finally with 163.0 mg Ti-BEA (prepared according to Blasco et al., *Chem Commun*, 1996, 2367-2368). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 0.922 mmol of methyl lactate is formed (35%) together with 0.028 mmol methyl 2-hydroxy-3-butenoate (1.4%).

Examples 10-14 illustrate a process for the conversion of sucrose in different solvents using Sn-BEA as the catalyst.

Example 10

An autoclave (50 cc microclave) is charged with 8.0 g of water, 0.2256 g of sucrose (0.6590 mmol), and 160.7 mg Sn-BEA (prepared according to U.S. Pat. No. 6,306,364). The autoclave is closed, charged with 20 bar of argon and heated to 160° C. After the temperature reaches 100° C., the mechanical stirrer is started (500 rpm) and the mixture is heated for 20 hours under these conditions. HPLC-analysis of the reaction mixture shows that 0.791 mmol of lactic acid is formed (30%).

Example 11

An autoclave (50 cc microclave) is charged with 8.0 g of ethanol, 0.2252 g of sucrose (0.6578 mmol), 118.9 mg naphthalene (internal standard) and finally with 160.0 mg Sn-BEA (prepared according to U.S. Pat. No. 6,306,364). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 1.03 mmol of ethyl lactate is formed (39%) together with 0.316 mmol ethyl 2-hydroxy-3-butenoate (16%).

Example 12

An autoclave (50 cc microclave) is charged with 8.0 g of 2-propanol, 0.2249 g of sucrose (0.6569 mmol), 119.7 mg naphthalene (internal standard) and finally with 159.7 mg Sn-BEA (prepared according to U.S. Pat. No. 6,306,364). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 0.68 mmol of isopropyl lactate is formed (26%) together with 0.237 mmol isopropyl 2-hydroxy-3-butenoate (12%).

Example 13

An autoclave (50 cc microclave) is charged with 8.0 g of 1-butanol, 0.2249 g of sucrose (0.6569 mmol), 121.0 mg naphthalene (internal standard) and finally with 160.5 mg Sn-BEA (prepared according to U.S. Pat. No. 6,306,364). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 0.68 mmol of n-butyl lactate is formed (26%) together with 0.164 mmol n-butyl 2-hydroxy-3-butenoate (8%).

Example 14

An autoclave (50 cc microclave) is charged with 8.05 g of methanol and 0.1988 g of water, 0.2252 g of sucrose (0.6578 mmol), 122.6 mg naphthalene (internal standard) and finally with 160.7 mg Sn-BEA (prepared according to U.S. Pat. No. 6,306,364). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 1.47 mmol of methyl lactate is formed (56%) together with 0.065 mmol methyl 2-hydroxy-3-butenoate (3%).

Example 15 illustrates the reuse potential of the Sn-BEA catalyst.

An autoclave (50 cc microclave) is charged with 16.07 g of methanol, 0.4504 g of sucrose (1.316 mmol), 115.2 mg naphthalene (internal standard) and finally with 320.8 mg Sn-BEA (prepared according to U.S. Pat. No. 6,306,364). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 3.158 mmol of methyl lactate is formed (60%) together with 0.0513 mmol methyl 2-hydroxy-3-butenoate (1.3%).

The used catalyst was dried at 100° C. overnight and calcined at 480° C. for 10 hours reached with a heating ramp of 2° C./min.

Of the original 320.8 mg of catalyst 0.2996 g was recovered after the calcination procedure. The 0.2996 g catalyst is charged in an autoclave (50 cc microclave) along with 14.94 g methanol, 0.1190 g naphthalene and 0.4206 g of sucrose. The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 3.293 mmol of methyl lactate is formed (67%) together with 0.0885 mmol methyl 2-hydroxy-3-butenoate (2.4%).

The regeneration procedure was repeated a $3^{rd}$, $4^{th}$ and a $5^{th}$ time.

In the $3^{rd}$ run 0.2665 g of catalyst is used along with 13.29 g methanol, 0.1229 g naphthalene and 0.3740 g sucrose. GC-analysis of the reaction mixture shows that 3.016 mmol of methyl lactate is formed (69%) together with 0.1180 mmol methyl 2-hydroxy-3-butenoate (3.6%). In the $4^{th}$ run 0.2328 g of catalyst is used along with 11.60 g methanol, 0.1207 g naphthalene and 0.3267 g sucrose. GC-analysis of the reaction mixture shows that 2.520 mmol of methyl lactate is formed (66%) together with 0.1088 mmol methyl 2-hydroxy-3-butenoate (3.8%). In the $5^{th}$ run 0.2157 g of catalyst is used along with 10.70 g methanol, 0.1238 g naphthalene and 0.3027 g sucrose. GC-analysis of the reaction mixture shows that 2.335 mmol of methyl lactate is formed (66%) together with 0.0902 mmol methyl 2-hydroxy-3-butenoate (3.4%).

Examples 16 and 17 illustrate a fixed-bed process for the conversion of fructose in methanol to give a mixture of methyl lactate and methyl 2-hydroxy-3-butenoate using Sn-BEA and TS-1.

Example 16

A plug flow reactor is charged with 1.0 g of Sn-BEA and pressurized with nitrogen. The reactor is heated to 170° C. and a feed consisting of 11.0 g of fructose dissolved in 500 ml of methanol is passed through the reactor at a rate of 1.0 ml/minute. The resulting methanol solution is collected and analyzed. Analysis of the fraction collected between the 2nd and 3rd hour by GC-MS (durene was used as external standard) shows that 31% methyl lactate is formed together with 7% methyl 2-hydroxy-3-butenoate.

Example 17

A plug flow reactor is charged with 3.0 g of TS-1 (1.53 wt % Ti). The reactor is heated to 170° C. and a feed consisting of 5.0 wt % of fructose in methanol is passed through the reactor at a rate of 0.50 ml/minute. The resulting methanol solution is collected and analyzed. Analysis of the fraction collected between the 1st and 2nd hour by GC-MS (durene was used as external standard) shows that 27.3% methyl lactate is formed together with 2.2% methyl 2-hydroxy-3-butenoate.

Example 18-21

Comparison Examples using conventional catalysts and are not intended as examples according the invention.

Example 18

An autoclave (50 cc microclave) is charged with 8.0 g of methanol, 0.2264 g of sucrose (0.6613 mmol), 118.7 mg naphthalene (internal standard) and finally with 162.0 mg Si-BEA (prepared according to Zhu et al., *J. Catal.*, 227, 2004, 1-10). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 0.046 mmol of methyl lactate is formed (7%). No methyl 2-hydroxy-3-butenoate was formed.

Example 19

An autoclave (50 cc microclave) is charged with 8.0 g of methanol, 0.2250 g of sucrose (0.6572 mmol), 119.1 mg naphthalene (internal standard) and finally with 159.7 mg Al-BEA (Si:Al 65:1, prepared according to Zhu et al., *J. Catal.*, 227, 2004, 1-10). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that no methyl lactate has formed.

Example 20

An autoclave (50 cc microclave) is charged with 8.0 g of methanol, 0.2251 g of sucrose (0.6575 mmol), 119.1 mg naphthalene (internal standard) and finally 160.0 mg of $SnO_2$ nanopowder (Sigma-Aldrich) is added. The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 0.105 mmol of methyl lactate is formed (4%). No methyl 2-hydroxy-3-butenoate was formed.

Example 21

An autoclave (50 cc microclave) is charged with 8.0 g of methanol, 0.2259 g of sucrose (0.6599 mmol), 117.7 mg naphthalene (internal standard) and finally with 7.4 mg $SnCl_4*5H_2O$ (0.021 mmol, same amount of tin is used as for the examples with Sn-Beta). The autoclave is closed, charged with 20 bar of argon and heated to 160° C. After the temperature reaches 100° C., the mechanical stirrer is started (500 rpm) and the mixture is heated for 20 hours under these conditions. GC-analysis of the reaction mixture shows that 0.607 mmol of methyl lactate is formed (23%). No methyl 2-hydroxy-3-butenoate was formed.

What is claimed is:

1. A process for the production of lactic acid and 2-hydroxy-3-butenoic acid or esters of lactic acid and esters of 2-hydroxy-3-butenoic acid by conversion of glucose, fructose, sucrose, xylose or glycolaldehyde dissolved in a solvent in presence of a solid Lewis acidic catalyst, wherein the catalyst is a zeotype material with Lewis acidic properties containing tetravalent metals selected from Sn, Pb, Ge, Ti, Zr and/or Hf incorporated in the framework.

2. A process of claim 1, wherein the zeotype material has a structure type BEA, MFI, MEL, MTW, MOR, LTL, FAU.

3. A process of claim 2, wherein the zeotype material has incorporated in its framework tetravalent Sn.

4. A process of claim 1, wherein the solvent is water.

5. A process of claim 1, wherein the solvent is selected from a $C_1$ to $C_4$ alcohol.

6. A process of claim 5, wherein the solvent further contains a secondary solvent.

\* \* \* \* \*